(12) United States Patent
Govari et al.

(10) Patent No.: US 8,326,402 B2
(45) Date of Patent: Dec. 4, 2012

(54) DISTORTION-IMMUNE POSITION TRACKING USING FREQUENCY EXTRAPOLATION

(75) Inventors: Assaf Govari, Haifa (IL); Alexander Goldin, Haifa (IL); Meir Bar-Tal, Zichron Ya'acov (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1064 days.

(21) Appl. No.: 11/465,920

(22) Filed: Aug. 21, 2006

(65) Prior Publication Data

US 2008/0125646 A1 May 29, 2008

(51) Int. Cl.
*A61B 5/00* (2006.01)

(52) U.S. Cl. ........... 600/424; 702/65; 324/225; 606/130

(58) Field of Classification Search ................ 600/424, 600/434, 407; 702/64, 65; 324/326, 207.12, 324/207.17, 207.22, 225, 318; 606/130; 322/22; 455/456.1

See application file for complete search history.

(56) References Cited

U.S. PATENT DOCUMENTS

| | | | | |
|---|---|---|---|---|
| 4,737,794 A * | 4/1988 | Jones | ........................... | 342/448 |
| 4,829,250 A * | 5/1989 | Rotier | ......................... | 324/225 |
| 5,391,199 A | 2/1995 | Ben-Haim | | |
| 5,443,489 A | 8/1995 | Ben-Haim | | |
| 5,654,864 A | 8/1997 | Ritter et al. | | |
| 6,147,480 A | 11/2000 | Osadchy et al. | | |
| 6,172,499 B1 * | 1/2001 | Ashe | ....................... | 324/207.12 |
| 6,239,724 B1 | 5/2001 | Doron et al. | | |
| 6,332,089 B1 | 12/2001 | Acker et al. | | |
| 6,373,240 B1 | 4/2002 | Govari | | |
| 6,427,079 B1 * | 7/2002 | Schneider et al. | ............ | 600/424 |
| 6,553,326 B1 * | 4/2003 | Kirsch et al. | .................... | 702/65 |
| 6,618,612 B1 | 9/2003 | Acker et al. | | |
| 6,653,831 B2 * | 11/2003 | Friend et al. | .................. | 324/244 |
| 6,690,963 B2 | 2/2004 | Ben-Haim et al. | | |

(Continued)

FOREIGN PATENT DOCUMENTS

WO WO 96/05768 A1 2/1996

OTHER PUBLICATIONS

Ochoa-Mayorga V.M. et al.: "Local Quaternion Weighted Difference Functions for Orientation Calibration on Electromagnetic Trackers"; Computational Advances in Multi-Sensor Adaptive Processing, 2005 1$^{st}$ IEEE International Workshop on Puerto Vallarta, Mexico; Dec. 13, 2005; pp. 233-236; Piscataway, NJ USA.

(Continued)

*Primary Examiner* — Long V. Le
*Assistant Examiner* — Amanda Lauritzen

(57) ABSTRACT

A method for tracking a position of an object includes generating alternating current (AC) magnetic fields at two or more frequencies in a vicinity of the object using at least one field generator. The AC fields are sensed using a field sensor associated with the object. Corresponding AC data points that are indicative of amplitudes and directions of the AC fields at the field sensor are produced, wherein at least some of the sensed AC fields are subject to a distortion. A dependence of the AC data points on the frequencies of the AC fields is extrapolated to a target frequency so as to determine the amplitudes and directions of the AC fields with a reduced level of the distortion. Position coordinates of the object relative to the at least one field generator are calculated responsively to the extrapolated data points.

21 Claims, 3 Drawing Sheets

U.S. PATENT DOCUMENTS

| | | |
|---|---|---|
| 6,755,816 B2 | 6/2004 | Ritter et al. |
| 6,762,600 B2 * | 7/2004 | Khalfin .................... 324/207.17 |
| 6,879,160 B2 * | 4/2005 | Jakab ........................... 324/318 |
| 6,980,921 B2 * | 12/2005 | Anderson et al. ............. 702/150 |
| 7,020,512 B2 * | 3/2006 | Ritter et al. ................... 600/434 |
| 7,542,869 B2 * | 6/2009 | Gandelsman et al. ........ 702/152 |
| 2002/0065455 A1 | 5/2002 | Ben-Haim et al. |
| 2003/0120150 A1 | 6/2003 | Govari |
| 2003/0135112 A1 * | 7/2003 | Ritter et al. .................. 600/424 |
| 2004/0068178 A1 | 4/2004 | Govari |
| 2004/0116803 A1 * | 6/2004 | Jascob et al. ................. 600/424 |
| 2004/0207389 A1 | 10/2004 | Nieminen |
| 2004/0220471 A1 * | 11/2004 | Schwartz ...................... 600/424 |
| 2004/0239314 A1 | 12/2004 | Govari |
| 2006/0293593 A1 * | 12/2006 | Govari et al. ................. 600/424 |
| 2007/0078334 A1 * | 4/2007 | Scully et al. .................. 600/424 |
| 2008/0067982 A1 * | 3/2008 | Dooley ............................ 322/22 |
| 2008/0231264 A1 * | 9/2008 | Krueger et al. ........... 324/207.22 |
| 2008/0309344 A1 * | 12/2008 | Larsen .......................... 324/326 |

OTHER PUBLICATIONS

EP Search Report dated Jan. 17, 2008—EP 07 25 3262.

* cited by examiner

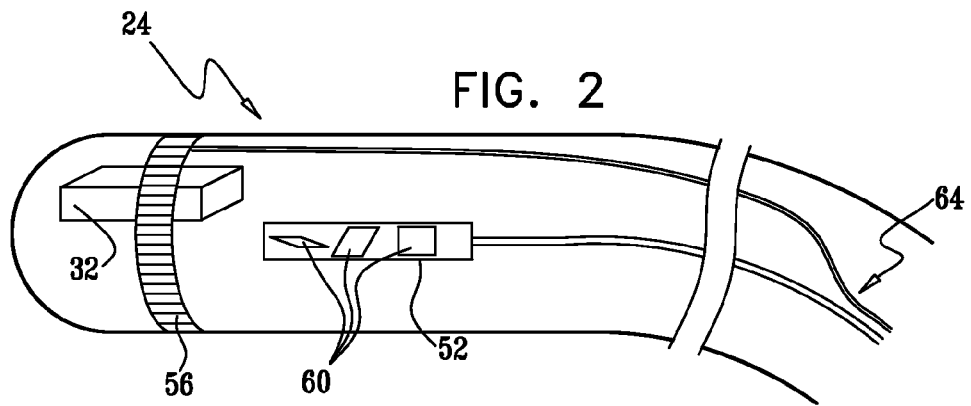
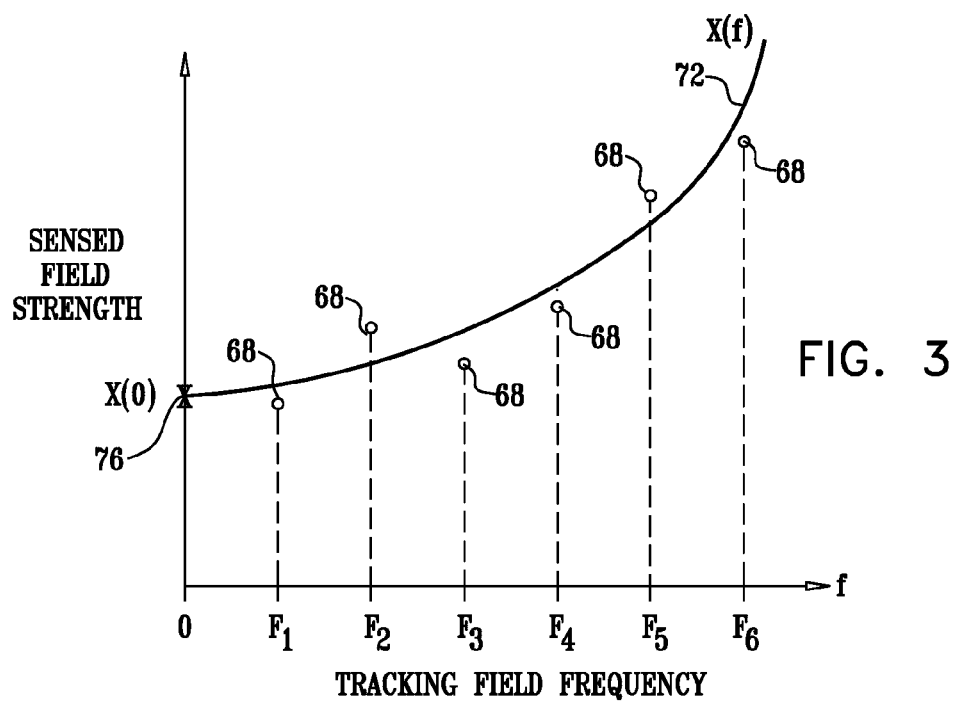

DISTORTION-IMMUNE POSITION TRACKING USING FREQUENCY EXTRAPOLATION

FIELD OF THE INVENTION

The present invention relates generally to magnetic position tracking systems, and particularly to methods and systems for performing accurate position measurements in the presence of field-distorting objects.

BACKGROUND OF THE INVENTION

Various methods and systems are known in the art for tracking the coordinates of objects involved in medical procedures. Some of these systems use magnetic field measurements. For example, U.S. Pat. Nos. 5,391,199 and 5,443,489, whose disclosures are incorporated herein by reference, describe systems in which the coordinates of an intrabody probe are determined using one or more field transducers. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations.

Additional methods and systems that relate to magnetic position tracking are also described, for example, in PCT Patent Publication WO 96/05768, U.S. Pat. Nos. 6,690,963, 6,239,724, 6,618,612 and 6,332,089, and U.S. Patent Application Publications 2002/0065455 A1, 2003/0120150 A1 and 2004/0068178 A1, whose disclosures are all incorporated herein by reference. These publications describe methods and systems that track the position of intrabody objects such as cardiac catheters, orthopedic implants and medical tools used in different medical procedures.

It is well known in the art that the presence of metallic, paramagnetic or ferromagnetic objects within the magnetic field of a magnetic position tracking system often distorts the system's measurements. The distortion is sometimes caused by eddy currents that are induced in such objects by the system's magnetic field, as well as by other effects.

Various methods and systems have been described in the art for performing position tracking in the presence of such interference. For example, U.S. Pat. No. 6,147,480, whose disclosure is incorporated herein by reference, describes a method in which the signals induced in the tracked object are first detected in the absence of any articles that could cause parasitic signal components. Baseline phases of the signals are determined. When an article that generates parasitic magnetic fields is introduced into the vicinity of the tracked object, the phase shift of the induced signals due to the parasitic components is detected. The measured phase shifts are used to indicate that the position of the object may be inaccurate. The phase shifts are also used for analyzing the signals so as to remove at least a portion of the parasitic signal components.

In some applications, the distortion of the magnetic field is measured and/or compensated for by conducting measurements using several magnetic field frequencies. For example, U.S. Pat. No. 4,829,250, whose disclosure is incorporated herein by reference, describes a magnetic system for determining the relative orientation between a fixed frame of reference and an unconstrained object. Mutual coupling between three orthogonally-disposed transmitting coils driven by a multi-frequency source and three orthogonal receiving coils produce sets of analog voltages. The analog voltages are sampled, digitized and processed using a Fast Fourier Transform (FFT) device to yield directional components for determining the pitch and yaw angles. By using the multi-frequency source to drive the transmitting coils and by deriving coordinate component measurements on at least two discrete frequencies, errors in the results due to eddy currents in surrounding conductive structures can be compensated for.

As another example, U.S. Pat. No. 6,373,240, whose disclosure is incorporated herein by reference, describes a method for tracking an object. The method includes producing an unperturbed energy field at a plurality of predetermined frequencies in the vicinity of the object, and determining a characteristic of a perturbing energy field induced responsively to the unperturbed field, due to the introduction of an article into the vicinity of the object. The method further includes receiving a plurality of resultant signals responsive to the unperturbed and perturbing energy fields generated at a location of the object after introduction of the article, determining an optimal frequency for the unperturbed energy field from amongst the plurality of predetermined frequencies responsive to a parameter of the resultant signals, and determining spatial coordinates of the object responsive to the resultant signal at the optimal frequency.

SUMMARY OF THE INVENTION

Embodiments of the present invention provide improved methods and systems for performing magnetic position tracking measurements in the presence of metallic, paramagnetic and/or ferromagnetic objects (collectively referred to as field-distorting objects) using frequency extrapolation.

The system comprises two or more field generators that generate magnetic fields in the vicinity of the tracked object. The magnetic fields are sensed by a position sensor associated with the object and converted to position signals that are used to calculate the position (location and orientation) coordinates of the object. The field generators generate alternating current (AC) magnetic fields at several frequencies. The frequency dependence of the measured field strengths is fitted and extrapolated to a target frequency, so as to reduce the effect of metal disturbance.

For example, the measurements may be extrapolated to zero frequency, so as to produce an equivalent direct current (DC) field strength. Unlike AC measurements, direct current (DC) magnetic fields generally do not cause eddy currents and other AC-related distortion. The equivalent DC field strength, which is substantially free of such distortion, is then used to calculate the position of the tracked object relative to the field generators. In alternative embodiments, the field strengths and/or coordinates are extrapolated to infinite frequency or any other target frequency, in order to cancel out metal distortion effects.

There is therefore provided, in accordance with an embodiment of the present invention, a method for tracking a position of an object, including:

using at least one field generator, generating alternating current (AC) magnetic fields at two or more frequencies in a vicinity of the object;

using a field sensor associated with the object, sensing the AC fields and producing corresponding AC data points that are indicative of amplitudes and directions of the AC fields at the field sensor, wherein at least some of the sensed AC fields are subject to a distortion;

extrapolating a dependence of the AC data points on the frequencies of the AC fields to a target frequency so as to determine the amplitudes and directions of the AC fields with a reduced level of the distortion; and calculating position coordinates of the object relative to the at least one field generator responsively to the extrapolated data points.

In some embodiments, the method includes inserting the object into an organ of a patient, and calculating the position coordinates of the object includes tracking the position of the object inside the organ. In an embodiment, the at least one field generator is associated with the object, and the field sensor is located externally to the organ.

In another embodiment, the distortion is caused by a field-distorting object subjected to at least some of the AC fields, and the object includes a material selected from a group consisting of metallic, paramagnetic and ferromagnetic materials.

In yet another embodiment, the target frequency includes a zero frequency. In still another embodiment, the target frequency includes an infinite frequency. Extrapolating the dependence may include fitting a function to the AC data points and the frequencies of the AC fields, and determining a value of the function at the target frequency.

In an embodiment, the function is selected from a group consisting of a polynomial function and a rational function, and fitting the function includes assigning values to coefficients of the function. Additionally or alternatively, extrapolating the dependence includes defining the function based on previously-acquired field measurements. Defining the function may include applying a principal components analysis (PCA) method to produce PCA base functions based on the previously-acquired field measurements and defining the function using the PCA base functions.

There is additionally provided, in accordance with an embodiment of the present invention, a system for tracking a position of an object, including:

at least one field generator, which is arranged to generate alternating current (AC) magnetic fields at two or more frequencies in a vicinity of the object;

a field sensor associated with the object, which is arranged to sense the AC fields and to produce corresponding AC data points that are indicative of amplitudes and directions of the AC fields at the field sensor, wherein at least some of the sensed AC fields are subject to a distortion; and a processor, which is arranged to extrapolate a dependence of the AC data points on the frequencies of the AC fields to a target frequency so as to determine the amplitudes and directions of the AC fields with a reduced level of the distortion, and to calculate position coordinates of the object relative to the at least one field generator responsively to the extrapolated data points.

There is also provided, in accordance with an embodiment of the present invention, a computer software product used in a system for tracking a position of an object, the product including a computer-readable medium, in which program instructions are stored, which instructions, when read by the computer, cause the computer to control at least one field generator so as to generate alternating current (AC) magnetic fields at two or more frequencies in a vicinity of the object, to accept from a field sensor associated with the object AC data points indicative of amplitudes and directions of the respective AC fields sensed by the field sensor, wherein at least some of the sensed AC fields are subject to a distortion, to extrapolate a dependence of the AC data points on the frequencies of the AC fields to a target frequency so as to determine the amplitudes and directions of the AC fields with a reduced level of the distortion, and to calculate position coordinates of the object relative to the at least one field generator responsively to the extrapolated data points.

The present invention will be more fully understood from the following detailed description of the embodiments thereof, taken together with the drawings in which:

BRIEF DESCRIPTION OF THE DRAWINGS

FIG. 2 is a schematic, pictorial illustration of a catheter, in accordance with an embodiment of the present invention;

FIG. 3 is a plot that schematically illustrates frequency extrapolation of measured field strength data, in accordance with an embodiment of the present invention.

DETAILED DESCRIPTION OF EMBODIMENTS

System Description

Figure 1:
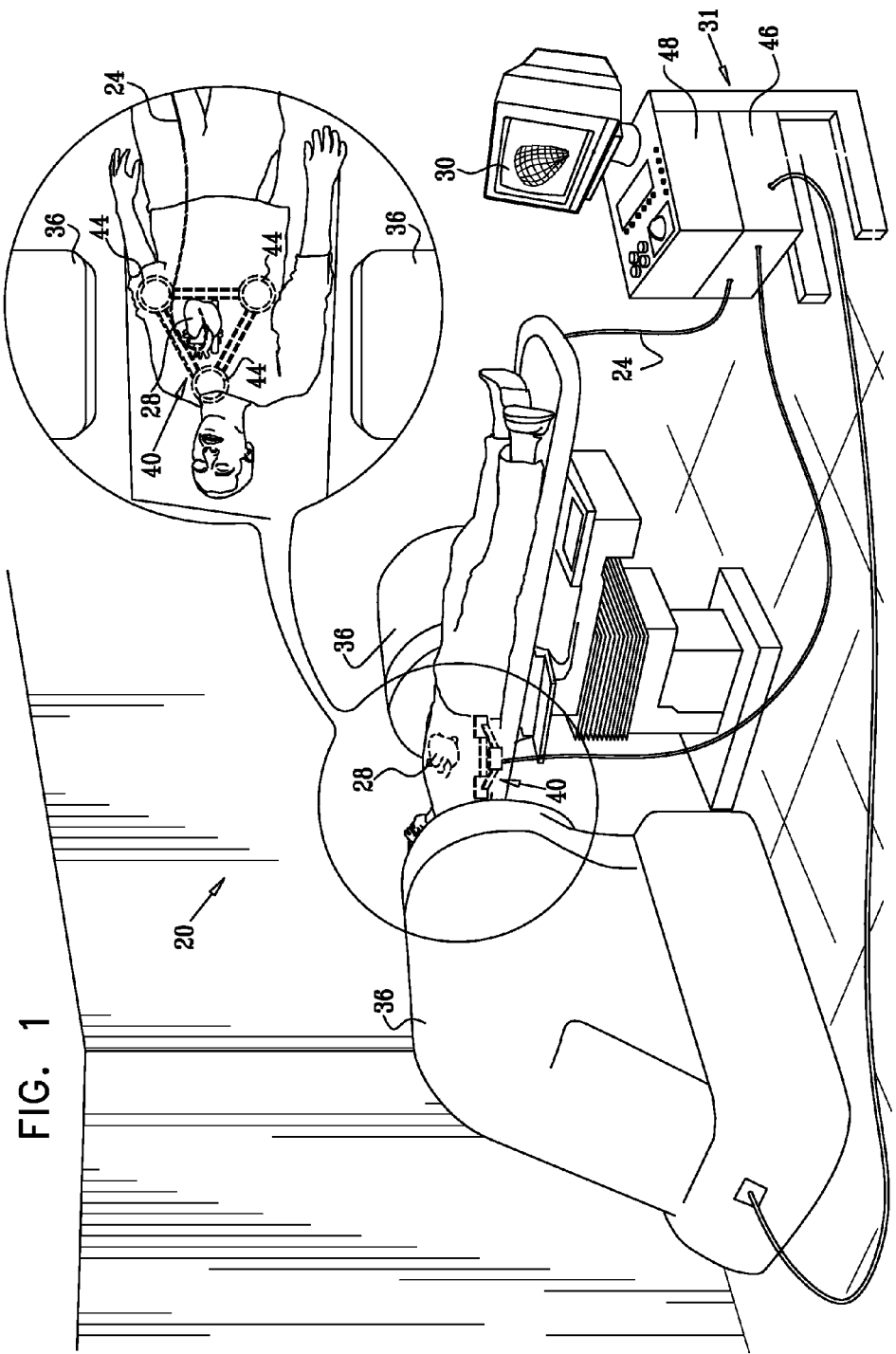
FIG. 1 is a schematic, pictorial illustration of a system for position tracking and steering of intrabody objects, in accordance with an embodiment of the present invention.

FIG. 1 is a schematic, pictorial illustration of a system 20 for position tracking and steering of intrabody objects, in accordance with an embodiment of the present invention. System 20 tracks and steers an intrabody object, such as a cardiac catheter 24, which is inserted into an organ, such as a heart 28 of a patient. System 20 also measures, tracks and displays the position (i.e., the location and orientation) of catheter 24. In some embodiments, the catheter position is registered with a three-dimensional model of the heart or parts thereof. The catheter position with respect to the heart is displayed to a physician on a display 30. The physician uses an operator console 31 to steer the catheter and to view its position during the medical procedure.

System 20 can be used for performing a variety of intra-cardiac surgical and diagnostic procedures in which navigation and steering of the catheter is performed automatically or semi-automatically by the system, and not manually by the physician. The catheter steering functions of system 20 can be implemented, for example, by using the Niobe® magnetic navigation system produced by Stereotaxis, Inc. (St. Louis, Mo.). Details regarding this system are available at www.stereotaxis.com. Methods for magnetic catheter navigation are also described, for example, in U.S. Pat. Nos. 5,654,864 and 6,755,816, whose disclosures are incorporated herein by reference.

System 20 positions, orients and steers catheter 24 by applying a magnetic field, referred to herein as a steering field, in a working volume that includes the catheter. An internal magnet is fitted into the distal tip of catheter 24. (Catheter 24 is shown in detail in FIG. 3 below.) The steering field steers (i.e., rotates and moves) the internal magnet, thus steering the distal tip of catheter 24.

The steering field is generated by a pair of external magnets 36, typically positioned on either side of the patient. In some embodiments, magnets 36 comprise electro-magnets that generate the steering field responsively to suitable steering control signals generated by console 31. In some embodiments, the steering field is rotated or otherwise controlled by physically moving (e.g., rotating) external magnets 36 or parts thereof. The difficulties that arise from having large metallic objects whose position may very over time, such as magnets 36, in close proximity to the working volume will be discussed hereinbelow.

System 20 measures and tracks the location and orientation of catheter 24 during the medical procedure. For this purpose, the system comprises a location pad 40. Location pad 40 comprises field generators, such as field generating coils 44. Coils 44 are positioned at fixed, known locations and orientations in the vicinity of the working volume. In the exemplary configuration of FIG. 1, location pad 40 is placed horizontally under the bed on which the patient lies. Pad 40 in this example has a triangular shape and comprises three coils 44. In alternative embodiments, location pad 40 may comprise any number of field generators arranged in any suitable geometrical configuration.

Console 31 comprises a signal generator 46, which generates drive signals that drive coils 44. In the exemplary embodiment of FIG. 1, three drive signals are generated. Each coil 44 generates an alternating current (AC) magnetic field, referred to herein as a tracking field, responsively to the respective drive signal driving it.

Signal generator 46 comprises a variable-frequency signal generator, which can be set to generate drive signals having frequencies within a predetermined range. System 20 performs field measurements at several frequencies in order to cancel out distortion effects introduced into the tracking fields, as will be explained below. Typically, the frequencies of the drive signals generated by signal generator 46 (and consequently the frequencies of the respective tracking fields) are in the range of several hundred Hz to several KHz, although other frequency ranges can be used as well.

A position sensor fitted into the distal tip of catheter 24 senses the tracking fields generated by coils 44 and produces respective position signals, which are indicative of the location and orientation of the sensor with respect to the field generating coils. The position signals are sent to console 31, typically along a cable running through catheter 24 to the console. Console 31 comprises a tracking processor 48, which calculates the location and orientation of catheter 24 responsively to the position signals. Processor 48 displays the location and orientation of the catheter, typically expressed as a six-dimensional coordinate, to the physician using display 30.

Processor 48 also controls and manages the operation of signal generator 46. In particular, processor 48 sets the appropriate frequencies for generating the different drive signals. In some embodiments, field-generating coils 44 are operated sequentially so that the position sensor measures the tracking field originating from a single coil 44 at any given time. In these embodiments, processor 48 alternates the operation of each coil 44 and associates the position signals received from the catheter with the appropriate field-generating coil.

Typically, tracking processor 48 is implemented using a general-purpose computer, which is programmed in software to carry out the functions described herein. The software may be downloaded to the computer in electronic form, over a network, for example, or it may alternatively be supplied to the computer on tangible media, such as CD-ROM. The tracking processor may be integrated with other computing functions of console 31.

In an alternative embodiment, field generators are fitted into the distal tip of catheter 24. The magnetic fields generated by the field generators are sensed by position sensors located at known positions outside the patient's body, such as in location pad 40. The sensed fields are used to determine the position of catheter 24.

FIG. 2 is a schematic, pictorial illustration of the distal tip of catheter 24, in accordance with an embodiment of the present invention. Catheter 24 comprises an internal magnet 32 and a position sensor 52, as described above. Catheter 24 may also comprise one or more electrodes 56, such as ablation electrodes and electrodes for sensing local electrical potentials. Position sensor 52 comprises field-sensing elements, such as field sensing coils 60. In some embodiments, position sensor 52 comprises three field-sensing coils 60 oriented in three mutually-orthogonal planes. Each coil 60 senses one of the three orthogonal components of the AC tracking field and produces a respective position signal responsively to the sensed component. Sensor 52 and electrodes 56 are typically connected to console 31 via cables 64 running through the catheter.

It is well known in the art that metallic, paramagnetic and ferromagnetic objects (collectively referred to herein as field-distorting objects) placed in an AC magnetic field cause distortion of the field in their vicinity. For example, when a metallic object is subjected to an AC magnetic field, eddy currents are induced in the object, which in turn produce parasitic magnetic fields that distort the AC magnetic field. Ferromagnetic objects distort the magnetic field by attracting and changing the density and orientation of the field lines.

In the context of a magnetic position tracking system, when a field-distorting object is present in the vicinity of position sensor 52, the tracking field sensed by sensor 52 is distorted, causing erroneous position measurements. The severity of the distortion generally depends on the amount of field-distorting material present, to its proximity to the position sensor and to the field generating coils, and/or to the angle in which the tracking field impinges on the field-distorting object. In the system of FIG. 1, for example, external magnets 36 typically contain a large mass of field-distorting material and are located in close proximity to the working volume. As such, external magnets 36 may cause a significant distortion of the tracking field sensed by the position sensor.

The methods and systems described hereinbelow are mainly concerned with performing accurate position tracking measurements in the presence of severe distortion of the tracking magnetic field. The catheter steering system of FIG. 1 is described purely as an exemplary application, in which objects located in or near the working volume of the position tracking system cause severe distortion of the tracking field.

However, embodiments of the present invention are in no way limited to magnetic steering applications. The methods and systems described herein can be used in any other suitable position tracking application for reducing such distortion effects. For example, the methods and systems described herein can be used to reduce field distortion effects caused by object such as C-arm fluoroscopes and magnetic resonance imaging (MRI) equipment.

In alternative embodiments, system 20 can be used to track various types of intrabody objects, such as endoscopes and orthopedic implants, as well as for tracking position sensors coupled to medical and surgical tools and instruments.

Distortion Reduction Using Frequency Extrapolation

In many cases, the distortion caused by field-distorting objects depends on the frequency of the tracking field. In some scenarios, there exists an optimal frequency in which the distortion is minimal. Some methods and systems, such as described, for example, in U.S. Pat. No. 6,373,240 cited above, scan the frequency range of the tracking field and search for such optimal frequency. However, when significant metal disturbance is present, such as in the presence of external magnets 36, severe distortion may be caused across the entire frequency range used by the system. Moreover, since magnets 36 are physically moved when steering the catheter, known a-priori distortion calibration and cancellation methods often cannot be applied.

In order to overcome these shortcomings of the prior art, embodiments of the present invention provide methods and systems for estimating and canceling the distortion of the tracking field caused by field-distorting objects.

The method described in FIGS. 3 and 4 below takes advantage of the fact that a direct current (DC) magnetic field, unlike an AC field, does not induce eddy currents in metallic objects, and is thus not distorted by the presence of such objects. On the other hand, a DC magnetic field also does not induce current in field sensing coils 60 of position sensor 52, and therefore cannot be sensed and measured by the position sensor.

The method of FIG. 4 below estimates an equivalent DC magnetic field strength by fitting and extrapolating a number of AC field measurements down to zero frequency (DC). The equivalent DC field strength, which is substantially free of distortion, is then used for calculating the position coordinates of the catheter. In an alternative embodiment described further below, the field measurements are extrapolated to infinite frequency to estimate a distortion-free field strength in the presence of ferromagnetic objects. Further alternatively, the frequency dependence of the field strength measurements can be extrapolated to any desired target frequency.

FIG. 3 is a plot that schematically illustrates frequency extrapolation of measured field strength data, in accordance with an embodiment of the present invention. Data points 68 correspond to a number of field strength measurements performed using a particular field-sensing coil 60 when sensing the AC tracking field generated by a particular field generating coil 44. As such, data points 68 are indicative of the amplitudes and directions of the tracking fields in the vicinity of the position sensor. In the example of FIG. 3, six measurements are taken at six respective tracking field frequencies denoted $F_1, \ldots, F_6$.

A curve 72 is fitted against data points 68. Curve 72 is the graphical representation of a function denoted X(f), which describes the field strength X as a function of frequency f. Methods for determining function X(f) are described in detail below. Curve 72 intercepts the vertical axis (corresponding to zero frequency, or DC) at an intercept point 76. The field strength value at the intercept point, or X(0), is an equivalent DC field strength estimate, which is substantially free of any distortion related to AC fields, such as eddy current distortion.

Figure 4:
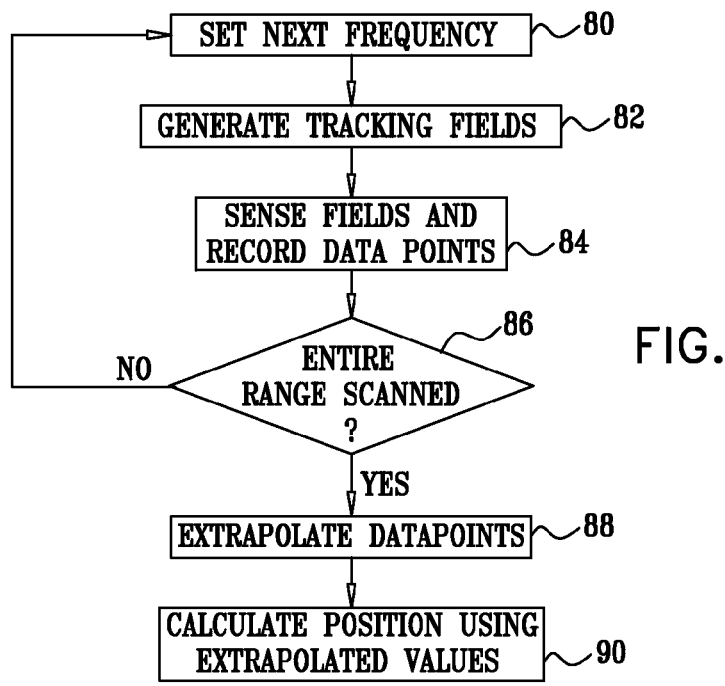
FIG. 4 is a flow chart that schematically illustrates a method for position tracking in the presence of field distortion, in accordance with an embodiment of the present invention.

FIG. 4 is a flow chart that schematically illustrates a method for position tracking in the presence of field distortion, in accordance with an embodiment of the present invention. At steps 80-86 below, system 20 performs multiple field strength measurements at catheter 24 using multiple frequencies selected from a predetermined frequency range. The frequency range often comprises a predetermined list of frequencies, although any other suitable method of defining the frequency range can also be used.

The method begins with processor 48 setting a frequency to be used for generating the tracking fields, at a frequency-setting step 80. Processor 48 selects a frequency from the range and sets signal generator 46 to generate drive signals having this frequency.

Signal generator 46 generates the drive signals and coils 44 generate the respective AC tracking fields, at a field generation step 82. Field sensing coils 60 in position sensor 52 of catheter 24 sense the tracking fields generated by coils 44, at a measurement step 84. Coils 60 produce position signals responsively to the sensed fields and the position signals are transmitted to console 31 via cables 64. Processor 48 receives the position signals and records the measured field strengths as data points associated with the tracking field frequency used.

As noted above, in some embodiments, coils 44 are operated sequentially at step 82. In these embodiments, the output of step 84 is a plurality of measured data points indicating the field strengths of the tracking field generated by each coil 44, as measured by each coil 60 at the particular frequency. For example, in the system configuration of FIG. 1 above, the output of step 84 comprises 3×3=9 data points in total.

Processor 48 checks whether all frequencies in the frequency range have been measured, at a range-checking step 86. If there are remaining frequencies to be measured, the method loops back to step 80 above.

Otherwise, processor 48 performs fitting and extrapolation of the measured data points. At this stage, processor 48 holds several sets of data points, such as the set shown in FIG. 3 above. Each set of data points corresponds to a pair of {field generating coil 44, field-sensing coil 60}. Each set comprises the field strengths generated by the particular coil 44, as measured by the particular coil 60, over the frequencies scanned at steps 80-86 above.

For each set of data points (i.e., for each pair of {coil 44, coil 60}), processor 48 fits and extrapolates the measured data, similarly to the description of FIG. 3 above, at an extrapolation step 88. In some embodiments, processor 48 fits a curve defined by a function X(f) to the data points. (See, for example, curve 72 fitted to data points 68 in FIG. 3 above.) Then, processor 48 estimates the extrapolated value of this function at zero frequency, i.e., X(0).

In some embodiments, X(f) comprises a polynomial function having the form $$X(f) = \sum_{i=0}^{m} a_i f^i,$$

wherein m denotes the rank of the polynomial X(f) and $a_0, \ldots, a_m$ are m+1 polynomial coefficients, which are fitted by processor 48 responsively to data points 68. Processor 48 can use any polynomial fitting method known in the art for determining the values of coefficients $a_0, \ldots, a_m$ such as a least squares (LS) method.

In some cases, however, estimating X(0) using polynomial fitting may not provide sufficient accuracy. In some embodiments, processor 48 fits data points 68 with a rational function (i.e., a ratio of two polynomials) having the form:

$$X(f) = \frac{\sum_{i=0}^{m} a_i f^i}{\sum_{i=0}^{n} b_i f^i} \qquad [1]$$

wherein the numerator and denominator of X(f) comprise two polynomial functions having ranks m and n and coefficients $a_0, \ldots, a_m$ and $b_0, \ldots, b_n$, respectively. Processor 48 may apply any suitable method known in the art for determining the coefficients $a_0, \ldots, a_m$ and $b_0, \ldots, b_n$. For example, in some embodiments, processor 48 may apply the well-known Padé approximation. Assuming that X(f) is sufficiently smooth, it is often possible to reach a good approximation of X(0) with relatively low rank polynomials (i.e., small values of m and n). Without loss of generality, by equivalent scaling of the numerator and denominator, it is possible to set $b_0=1$. After setting $b_0=1$, the equivalent DC field strength value is given by $X(0)=a_0$.

In alternative embodiments, processor 48 may construct function $X(f)$ based on previously-acquired field measurements in the presence of field-distorting objects. Typically, the previous measurements comprise measurements at different frequencies, including the target frequency, to which the data points are to be extrapolated. In many cases, extrapolating the measured data using previously-acquired field measurements often produces higher-accuracy extrapolation results in comparison to using polynomials or rational functions.

The processor may use different training methods in order to extrapolate the measured data points to the target frequency, based on the information carried by the previously-acquired field measurements. For example, processor 48 may use methods based on neural networks for this purpose.

In some embodiments, processor 48 uses the previously-acquired measurements to define a set of base functions. The processor then calculates a function $X(f)$, which is spanned by the base functions and best fits the measured data. For example, processor 48 may calculate the base functions using principal components analysis (PCA) methods. PCA is a well-known statistical analysis technique, which is described, for example, by Smith in "A Tutorial on Principal Components Analysis," Cornell University, Ithaca, N.Y., Feb. 26, 2002, which is incorporated herein by reference. When using PCA, processor 48 calculates a set of orthogonal PCA base functions and fits a function $X(f)$, which spanned by the PCA base functions and best fits the measured data.

As noted above, processor 48 performs the fitting and extrapolation process of step 88 for every pair of {coil 44, coil 60}. The output of step 88 is a plurality of equivalent DC field strength values (i.e., $X(0)$ values), which are substantially free of distortion.

In an alternative embodiment, processor 48 may combine the field measurements of all three field-sensing coils 60, and fit and extrapolate them together. This approach may be preferable, for example, when the field measurements of one of coils 60 have a poor signal-to-noise ratio.

Processor 48 now calculates the position (location and orientation) coordinates of position sensor 52, at a position calculation step 90. Processor 48 uses the equivalent DC estimates as corrected position signals, to calculate the location and orientation coordinates of sensor 52, and consequently of the distal tip of catheter 24.

In some scenarios, the field-distorting object that distorts the tracking field comprises high ferromagnetic material content. Ferromagnetic material effects, unlike eddy current related effects, persist at zero frequency. On the other hand, the effect of ferromagnetic materials on the position measurements typically diminishes at frequencies above a certain cutoff frequency. Therefore, when ferromagnetic objects are a significant source of distortion in the position measurements of the system, processor 48 may extrapolate function $X(f)$ to infinite frequency, rather than to zero frequency. The asymptotic value of $X(f)$ at infinity is then used as the distortion-corrected value.

Further alternatively, the frequency dependence of the field strength measurements can be extrapolated or interpolated using the methods described herein to any other suitable target frequency.

Although the embodiments described herein mainly refer to improving the distortion immunity of medical position tracking and steering systems, these methods and systems can be used in additional applications, such as for reducing the distortion caused by the operating room table, fluoroscopy equipment, MRI equipment and/or any other field-distorting object.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for tracking a position of an object in the presence of a metal distortion, comprising:
   establishing a predetermined frequency range;
   using at least one field generator, generating alternating current (AC) magnetic fields at two or more frequencies in the predetermined frequency range in a vicinity of the object;
   using a field sensor associated with the object, sensing the AC fields and producing corresponding AC data points that are indicative of amplitudes and directions of the AC fields at the field sensor in the predetermined frequency range, wherein at least some of the sensed AC fields are subject to the metal distortion;
   extrapolating a dependence of the AC data points on the frequencies of the AC fields and fitting to a target frequency within the predetermined frequency range so as to determine the amplitudes and directions of the AC fields with a reduced level of the metal distortion, wherein the target frequency corresponds to an equivalent DC field strength that is substantially free of metal distortion; and
   calculating position coordinates of the object relative to the at least one field generator responsively to the extrapolated data points based on the equivalent DC field strength.

2. The method according to claim 1, and comprising inserting the object into an organ of a patient, wherein calculating the position coordinates of the object comprises tracking the position of the object inside the organ.

3. The method according to claim 2, wherein the at least one field generator is associated with the object, and wherein the field sensor is located externally to the organ.

4. The method according to claim 1, wherein the distortion is caused by a field-distorting object subjected to at least some of the AC fields, and wherein the object comprises a material selected from a group consisting of metallic, paramagnetic and ferromagnetic materials.

5. The method according to claim 1, wherein the target frequency comprises a zero frequency.

6. The method according to claim 1, wherein the target frequency comprises an infinite frequency.

7. The method according to claim 1, wherein extrapolating the dependence comprises fitting a function to the AC data points and the frequencies of the AC fields, and determining a value of the function at the target frequency.

8. The method according to claim 7, wherein the function is selected from a group consisting of a polynomial function and a rational function, and wherein fitting the function comprises assigning values to coefficients of the function.

9. The method according to claim 7, wherein extrapolating the dependence comprises defining the function based on previously-acquired field measurements.

10. The method according to claim 9, wherein defining the function comprises applying a principal components analysis (PCA) method to produce PCA base functions based on the previously-acquired field measurements and defining the function using the PCA base functions.

11. A system for tracking a position of an object in the presence of a metal disturbance, comprising:
   at least one field generator, which is configured to generate alternating current (AC) magnetic fields at two or more frequencies within a predetermined frequency range in a vicinity of the object;
   a field sensor associated with the object, which is configured to sense the AC fields and to produce corresponding AC data points that are indicative of amplitudes and directions of the AC fields at the field sensor in the predetermined frequency range, wherein at least some of the sensed AC fields are subject to the metal distortion, wherein the target frequency corresponds to an equivalent DC field strength within the predetermined frequency range that is substantially free of metal distortion; and
   a processor, having the predetermined frequency stored therein and which is configured to extrapolate a dependence of the AC data points on the frequencies of the AC fields and fit to a target frequency so as to determine the amplitudes and directions of the AC fields with a reduced level of the metal distortion, and to calculate position coordinates of the object relative to the at least one field generator responsively to the extrapolated data points based on the equivalent DC field strength.

12. The system according to claim 11, wherein the object is adapted to be inserted into an organ of a patient, and wherein the processor is configured to track the position of the object inside the organ.

13. The system according to claim 12, wherein the at least one field generator is associated with the object, and wherein the field sensor is located externally to the organ.

14. The system according to claim 11, wherein the distortion is caused by a field-distorting object subjected to at least some of the AC fields, and wherein the object comprises a material selected from a group consisting of metallic, paramagnetic and ferromagnetic materials.

15. The system according to claim 11, wherein the target frequency comprises a zero frequency.

16. The system according to claim 11, wherein the target frequency comprises an infinite frequency.

17. The system according to claim 11, wherein the processor is configured to fit a function to the AC data points and the frequencies of the AC fields, and to determine a value of the function at the target frequency.

18. The system according to claim 17, wherein the function is selected from a group consisting of a polynomial function and a rational function, and wherein the processor is configured to fit the function by assigning values to coefficients of the function.

19. The system according to claim 17, wherein the processor is configured to define the function based on previously-acquired field measurements.

20. The system according to claim 19, wherein the processor is configured to apply a principal components analysis (PCA) method to produce PCA base functions based on the previously-acquired field measurements, and to define the function using the PCA base functions.

21. A system for tracking a position of an object in the presence of a metal disturbance, the system comprising at least one field generator and field sensor and a processor having a predetermined frequency range stored therein, the processor configured to control the at least one field generator so as to generate alternating current (AC) magnetic fields at two or more frequencies in the predetermined frequency range in a vicinity of the object,
   to accept from the field sensor associated with the object AC data points indicative of amplitudes and directions of the respective AC fields sensed by the field sensor, wherein at least some of the sensed AC fields are subject to the metal distortion, to extrapolate a dependence of the AC data points on the frequencies of the AC fields and fit to a target frequency so as to determine the amplitudes and directions of the AC fields with a reduced level of the metal distortion, wherein the target frequency corresponds to an equivalent DC field strength within the predetermined frequency range that is substantially free of metal distortion; and
   to calculate position coordinates of the object relative to the at least one field generator responsively to the extrapolated data points based on the equivalent DC field strength.

* * * * *